United States Patent [19]

La Pierre et al.

[11] 4,430,516

[45] Feb. 7, 1984

[54] CONVERSION OF OLEFINS TO LOW POUR POINT DISTILLATES AND LUBES

[75] Inventors: Rene B. La Pierre, Medford, N.J.; Stephen S. Wong, Langhorne, Pa.

[73] Assignee: Mobil Oil Corporation, New York, N.Y.

[21] Appl. No.: 390,099

[22] Filed: Jun. 21, 1982

[51] Int. Cl.³ .............................................. C07C 2/02
[52] U.S. Cl. ................................................. 585/533
[58] Field of Search ................. 585/533; 208/DIG. 2

[56] References Cited

U.S. PATENT DOCUMENTS

| | | |
|---|---|---|
| 3,140,249 | 7/1964 | Plank et al. . |
| 3,140,253 | 7/1964 | Plank et al. . |
| 3,442,795 | 5/1969 | Kerr et al. ................... 208/DIG. 2 |
| 3,556,988 | 1/1971 | Stover et al. . |
| 3,928,483 | 12/1975 | Chang et al. . |
| 3,960,978 | 6/1976 | Givens et al. ........................ 585/533 |
| 3,979,472 | 3/1976 | Butter . |
| 4,013,732 | 3/1977 | Chang et al. . |
| 4,035,430 | 7/1977 | Dwyer et al. . |
| 4,058,576 | 11/1977 | Chang et al. . |
| 4,138,440 | 2/1979 | Chang et al. . |
| 4,138,442 | 2/1979 | Chang et al. . |
| 4,156,698 | 5/1979 | Dwyer et al. . |
| 4,254,295 | 3/1981 | Tabak ................................ 585/533 |

OTHER PUBLICATIONS

Adv. Catal. 18, 259 (1968).

Primary Examiner—Curtis R. Davis
Attorney, Agent, or Firm—Alexander J. McKillop; Michael G. Gilman; Charles J. Speciale

[57] ABSTRACT

A process for the conversion of olefins to distillate range hydrocarbons comprising contacting olefins with large pore zeolites.

7 Claims, No Drawings

CONVERSION OF OLEFINS TO LOW POUR POINT DISTILLATES AND LUBES

BACKGROUND OF THE INVENTION

This invention relates to a process for effecting the conversion of olefins to distillate range hydrocarbons and more particularly to improvements in the zeolite catalytic conversion of olefins to produce $C_{10}+$ hydrocarbons.

With the advent of fossil fuel shortages and the accelerated demand for petroleum derived products, there has been an ever increasing demand for synthetic means of providing hydrocarbons, useful as fuel components.

Recently, much effort has been devoted to the synthetic conversion of alcohols, such as methanol, to gasoline range hydrocarbons. One means which has proven successful involves the use of zeolites as catalysts for such conversion reactions. Among these processes are those disclosed in U.S. Pat. Nos. 3,928,483, 4,138,442, 4,013,732, 4,138,440, 3,979,472, and 4,035,430. Others include U.S. Pat. No. 4,156,698 which discloses employing an improved zeolite catalyst in a rare-earth matrix in the conversion process. Moreover, U.S. Pat. No. 4,058,576 discloses a method wherein alcohols are converted to olefins in the presence of zeolite catalysts and subsequently wherein these olefins are converted to gasoline boiling range components in the presence of certain zeolites.

Concomitant with the shortage of fossil fuel and the rising costs of gasoline, utilization of low pour point distillates, i.e. diesel fuels and lubricating oils, has been ever increasing too. Accordingly, recent efforts have been given to the development of improved processes for the production and upgrading of diesel fuel and lube products. While definite advances have been made in the production and upgrading of these type products, further processes are obviously welcome.

SUMMARY OF THE INVENTION

Accordingly, it is one object of the present invention to provide a process for the production of distillate and lube range ($C_{10}+$) hydrocarbons.

Another object of this invention to provide a novel process for the conversion of olefins to distillate and lube range hydrocarbons.

A further object of this invention is to provide a simple and direct one-step process for the production of distillate and lube range hydrocarbons from olefins.

A still further object of the present invention is to provide a process for the production of distillate and lube range hydrocarbon products which are suitable as diesel fuel, jet fuels and lubricating oils.

These and other objects are achieved herein by a process which comprises contacting a feed comprising an olefin, a mixture of olefins or a mixture of olefins and other hydrocarbon types, such as paraffins, with a high $SiO_2/Al_2O_3$ ratio large pore zeolite catalyst, under conditions of temperature and pressure sufficient to product $C_{10}+$ hydrocarbons.

DETAILED DESCRIPTION OF THE INVENTION

In accordance with the present invention, it has been surprisingly discovered that olefins can be converted to distillate range ($C_{10}+$) hydrocarbons by contact with large pore zeolite catalysts under certain conditions of temperature and pressure.

Thus, for the purpose of this invention, olefin rich feeds comprising light olefins, for example $C_2$-$C_{10}$ may be used as starting material to be converted by the process herein. More specifically, among the olefins contemplated as feed herein are included olefins having from $C_2$ to about $C_{10}$ carbon atoms. Moreover, mixtures of these olefins may be used as well as mixtures of these olefins and paraffins. Particularly preferred olefin feeds are comprised of olefins having from $C_2$ to about $C_6$ carbon atoms.

The zeolite catalysts which are employed in the present process are generally defined as large pore zeolites having pore dimensions greater than about 6 angstrom units and pore windows of about a size such as would be provided by 12-membered rings of oxygen atoms.

The zeolites useful in the present process have a structure which provides access to larger molecules. Rather than attempt to judge from crystal structure whether or not a catalyst possesses the necessary access, a simple determination of the "constraint index" may be made by continuously passing a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly space velocity (i.e. 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of hexane remaining})}{\log_{10}(\text{fraction of 3-methylpentane remaining})}$$

The constraint index approximates the ratio of the cracking rate constants for the two hydrocarbons.

Catalysts suitable for the present invention are those having a constraint index of about 0.5 to less than 2.

Representative crystalline aluminosilicates suitable for the present invention include those natural and synthetic crystalline aluminosilicates having uniform pores of a diameter preferably greater than about 6 angstrom units. Such crystalline aluminosilicates include zeolites Y, X, beta, L, ZSM-4, ZSM-20, as well as naturally occuring zeolites including faujasite, mordenite, offretite, gmelinite, and the like. Preferred crystalline aluminosilicates include those having a high $SiO_2/Al_2O_3$ ratio, typified by zeolite Beta and dealuminized Y and mordenite. High $SiO_2/Al_2O_3$ ratio large pore zeolites are preferred since they reduce catalyst aging. Ratios of from about 7:1 to about 1000:1 are contemplated.

The crystalline aluminosilicates employed herein are essentially characterized by a high catalytic activity.

This high catalytic activity may be imparted to the catalyst particles by base exchanging alkali metal aluminosilicate particles with a base-exchange solution containing ions selected from the group consisting of cations of elements of Group IB-VIII of the Periodic Table, hydrogen, and hydrogen precursors, including mixtures thereof with one another. Hydrogen precursors, such as ammonia and ammonium salts, typically undergo, upon heating, degradation to hydrogen cations in contact with aluminosilicates. Suitable methods of base exchange are described in U.S. Pat. Nos. 3,140,249 and 3,140,253.

Where an alkali metal aluminosilicate is employed initially, it is essential to base exchange either the aluminosilicate particles to reduce the sodium content of the final product to less than about 4% by weight and preferably less than 1% by weight.

As previously discussed, base exchange may be accomplished by one or more contacts with a solution containing ions selected from the group consisting of cations of the elements of Groups IB-VIII, hydrogen and hydrogen precursors, including mixtures thereof with one another.

Water is the preferred solvent for the cationic salt for reasons of economy and ease of preparation in large scale operations involving continuous or batchwise treatment. Similarly, for this reason, organic solvents are less preferred but can be employed providing the solvent permits ionization of the cationic salt. Typical solvents include cyclic and acylic ethers such as dioxane, tetrahydrofuran, diethyl ether, diisopropyl ether, and the like; ketones, such as acetone and methyl ethyl ketone; esters such as ethyl acetate; alcohols such as ethanol, propanol, butanol, etc.; and miscellaneous solvents such as dimethylformamide, and the like.

In carrying out the treatment with the fluid medium, the procedure employed varies depending upon the particular aluminosilicate which is treated. If the aluminosilicate which is treated has alkali metal cations associated therewith, then the treatment with the fluid medium or media should be carried out until such time as the alkali metal cations originally present are substantially exhausted. Alkali metal cations, if present in the treated aluminosilicate, tend to suppress or limit catalytic properties, the activity of which, as a general rule, decreases with increasing content of these metallic cations. On the other hand, if the aluminosilicate which is treated with the desired fluid medium is substantially free of alkali metal cations, i.e., a calcium aluminosilicate, then the treatment need not be carried out until such time as the metal is exhausted since the presence of metals other than alkali metals does not seriously limit catalytic properties. Effective treatment with the fluid medium to obtain a modified aluminosilicate having high catalytic activity will vary, of course, with the duration of the treatment and the temperature at which the treatment is carried out. Elevated temperatures tend to hasten the speed of treatment whereas the duration thereof varies inversely with the general concentration of ions in the fluid medium. In general, the temperatures employed range from below ambient room temperature of 24° C. up to temperatures below the decomposition temperature of the aluminosilicate. Following the fluid treatment, the treated aluminosilicate is washed with water, preferably distilled water, until the effluent wash water has a pH value of wash water, i.e., between 5 and 8. The aluminosilicate materials is thereafter analyzed for metallic content by methods well known in the art.

Analysis also involves analyzing the effluent wash for anions obtained in the wash as a result of the treatment, as well as determination of and correction for anions that pass into the effluent wash from soluble substances, or decomposition products of insoluble substances, which are otherwise present in the aluminosilicate as impurities.

The treatment of the aluminosilicate with the fluid medium or media may be accomplished in a batchwise or continuous method under atmospheric, superatmospheric or subatmospheric pressures. A solution of rare earth metal cations in the form of a molten material, vapor, aqueous or non-aqueous solution may be passed slowly through a fixed bed of aluminosilicate. If desired, hydrothermal treatment or corresponding non-aqueous treatment with polar solvents may be effected by introducing the aluminosilicate and fluid medium into a closed vessel maintained under autogeneous pressure. Similarly, treatments involving fusion or vapor phase contact may be employed.

Aluminosilicates which are treated with a fluid medium or media in the manner above described include a wide variety of aluminosilicates both natural and synthetic which have a crystalline or combination of crystalline and amorphous structure.

The aluminosilicates can be described as a three-dimensional framework of $SiO_4$ and $AlO_4$ tetrahedra in which the tetrahedra are cross-linked by the sharing of oxygen atoms whereby the ratio of total aluminum and silicon atoms to oxygen atoms is 1:2. In their hydrated form, the aluminosilicates may be represented by the formula:

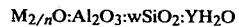

$$M_{2/n}O:Al_2O_3:wSiO_2:YH_2O$$

wherein M represents at least one cation which balances the electrovalence of the tetrahedra, n represents the valence of the cation, w the moles of $SiO_2$ and Y the moles of $H_2O$. The cations can be any or more of a number of metal ions, depending upon whether the aluminosilicate is synthesized or occurs naturally. Typical cations include sodium, lithium, potassium, silver, magnesium, calcium, zinc, barium, iron, nickel, cobalt and manganese. Although the proportions of inorganic oxides in the silicates and their spatial arrangements may vary affecting distinct properties in the aluminosilicate, the main characteristic of these materials is their ability to undergo dehydration without substantially affecting the $SiO_4$ and $AlO_4$ framework.

Aluminosilicates falling within the above formula are well known and, as noted, include synthesized aluminosilicates, natural aluminosilicates, and certain caustic treated clays. Among the aluninosilicates are included zeolites, Y, L, S, X, levynite, erionite, faujasite, analcite, paulingite, noselite, phillipsite, datolite, gmelinite leucite, scapolite, mordenite as well as certain caustic treated clays such as montmorillonite and kaolin families. The preferred aluminosilicates are those having pore diameters of greater than about 6 angstroms.

It has been discovered herein that certain conditions of temperature and pressure are essential to the conversion of the olefin feed to distillate range hydrocarbons. That is, it has been found herein that the conversion to distillate range hydrocarbons takes place under conditions of elevated pressure and relatively low temperature. More particularly, the elevated pressures contemplated within the scope of the present invention are within the range of from about 200 psig to about 2000 psig, preferably from about 500 to about 1500 psig, while the temperatures found essential to the conversion are from about 200°–750° F. and preferably from about 300° to about 650° F.

Typically, in carrying out the process of the present invention, the olefin feed is brought into contact with the hereinbefore described large pore zeolite catalysts at a temperature in the range of from about 300°–650° F. for a contact time equivalent to or the same as a weight hourly space velocity (WHSV) of about 20 to about 0.1, preferably about 5 to about 0.5, it being understood that WSHV signifies pounds of feed per pound of zeolite per hour; and at a pressure as recited above. The conversion can be carried out with or without a diluent gas (such as hydrogen or nitrogen).

The distillate range products resulting from the present process comprise 330° F. to about 650° F. distillate products ranging from kerosene to diesel fuels, jet fuels and the like as well as 650° F.+ lube products.

In order that those skilled in the art may better understand how the present invention may be practiced, the following examples are given by way of illustration and not by way of limitation.

EXAMPLE

Propylene is converted over a dealuminized Y(SiO$_2$/Al$_2$O$_3$=75) zeolite at 510° F., 1000 psig, 1 WHSV and N$_2$/HC ratio of 1. The results are tabulated below:

TABLE

|  | Wt. % in Liquid Product |
|---|---|
| IBP to about 330° F. Naphtha | 19.8 |
| 330° to about 650° F. distillate | 68.3 |
| 650° F.+ lube | 9.1 |

Substituting other large pore zeolite catalysts and other olefins, such as Beta and hexene respectively, provides similar conversion results.

The process of the present invention provides a particularly desirable alternative to refiners for the increased production of distillates and lubes, especially in the situation where increased amounts of light olefins are produced as a result of more severe FCC operations.

What is claimed is:

1. A process for the conversion of olefins to distillate and the range (C$_{10}$+) hydrocarbons, said process comprising contacting an olefin feed with a high SiO$_2$/Al$_2$O$_3$ ratio large pore crystalline aluminosilicate zeolite catalyst at a pressure in the range of from about 200 psig to about 2000 psig and at a conversion temperature in the range of from about 200°–750° F. and weight hourly space velocity of about 20 to 0.1 wherein the large pore crystalline aluminosilicate zeolite catalyst has pore dimensions of greater than about 6 angstroms and a constraint index of about 0.5 to less than 2.

2. A process as defined in claim 1 wherein said feed comprises an olefin, a mixture of olefins or a mixture of olefins and paraffins.

3. A process as defined in claim 1 wherein said large pore crystalline aluminosilicate zeolite catalyst has a SiO$_2$/Al$_2$O$_3$ ratio of from about 7:1 to about 1000:1.

4. A process as defined in claim 1 wherein said olefin is propylene.

5. A process as defined in claim 1 wherein said temperature is from about 300° F. to 650° F. and said pressure is from about 500 psig to 1500 psig.

6. A process for the conversion of propylene to distillate range (C$_{10}$+) hydrocarbons, said process comprising contacting propylene with a high SiO$_2$/Al$_2$O$_3$ ratio large pore crystalline aluminosilicate zeolite catalyst at a pressure in the range of from about 500 psig to about 1500 psig and at a conversion temperature of from about 300° F. to about 650° F. wherein the large pore crystalline aluminosilicate zeolite catalyst has pore dimensions of greater than about 6 angstroms and a constraint index of about 0.5 to less than 2.

7. A process as defined in claim 6 wherein said zeolite catalyst is a dealuminized Y zeolite having a SiO$_2$/Al$_2$O$_3$ ratio of about 75.

* * * * *

UNITED STATES PATENT AND TRADEMARK OFFICE
CERTIFICATE OF CORRECTION

PATENT NO. : 4,430,516
DATED : February 7, 1984
INVENTOR(S) : R.B. LaPierre and S.S. Wong It is certified that error appears in the above-identified patent and that said Letters Patent is hereby corrected as shown below:

Column 6, line 5 (Claim 1) - after "distillate and" delete "the" and insert --lube--.

Signed and Sealed this

First Day of January 1985

[SEAL]

Attest:

GERALD J. MOSSINGHOFF

Attesting Officer  Commissioner of Patents and Trademarks